(12) United States Patent
DeGroot et al.

(10) Patent No.: US 8,170,663 B2
(45) Date of Patent: May 1, 2012

(54) METHOD AND APPARATUS TO CONTROL DELIVERY OF HIGH-VOLTAGE AND ANTI-TACHY PACING THERAPY IN AN IMPLANTABLE MEDICAL DEVICE

(75) Inventors: Paul J. DeGroot, Brooklyn Park, MN (US); Kevin T. Ousdigian, St. Paul, MN (US); Vasant Padmanabhan, Maple Grove, MN (US); Paul Krause, St. Louis Park, MN (US); Vinod Sharma, Roseville, MN (US)

(73) Assignee: Medtronic, Inc., Minneapolis ( * ) Notice: Subject to any disclaimer, the term of this patent is extended or adjusted under 35 U.S.C. 154(b) by 744 days.

(21) Appl. No.: 11/687,282

(22) Filed: Mar. 16, 2007

(65) Prior Publication Data
US 2007/0156189 A1 Jul. 5, 2007

Related U.S. Application Data

(63) Continuation of application No. 10/810,449, filed on Mar. 26, 2004, now abandoned, which is a continuation of application No. 09/918,224, filed on Jul. 30, 2001, now Pat. No. 6,718,204.

(51) Int. Cl.
*A61N 1/362* (2006.01)
*A61N 1/39* (2006.01)
(52) U.S. Cl. .................. 607/4; 607/16; 607/34
(58) Field of Classification Search ............. 607/4, 6, 607/16, 34, 5, 14, 12, 9
See application file for complete search history.

(56) References Cited

U.S. PATENT DOCUMENTS

| | | | |
|---|---|---|---|
| 4,407,288 A | 10/1983 | Langer et al. |
| 4,428,378 A | 1/1984 | Anderson et al. |
| 4,821,723 A | 4/1989 | Baker, Jr. et al. |
| 4,830,006 A | 5/1989 | Haluska et al. |
| 4,865,036 A | 9/1989 | Chirife |
| 4,949,719 A | 8/1990 | Pless et al. |
| 4,967,747 A | 11/1990 | Carroll et al. |
| 5,048,521 A | 9/1991 | Pless et al. |
| 5,107,850 A | 4/1992 | Olive |
| 5,161,527 A | 11/1992 | Nappholz et al. |
| 5,176,137 A | 1/1993 | Erickson et al. |
| 5,191,884 A | 3/1993 | Gilli et al. |
| 5,193,535 A | 3/1993 | Bardy et al. |
| 5,193,536 A | 3/1993 | Mehra |
| 5,205,583 A | 4/1993 | Henseler et al. |
| 5,209,229 A | 5/1993 | Gilli |
| 5,215,083 A | 6/1993 | Drane et al. |

(Continued)

*Primary Examiner* — Carl H Layno
*Assistant Examiner* — Natasha Patel
(74) *Attorney, Agent, or Firm* — Michael C. Soldner

(57) ABSTRACT

A system and method for delivering both anti-tachy pacing (ATP) therapy and high-voltage shock therapy in response to detection of abnormal cardiac rhythms is disclosed. The system controls the time between delivering ATP therapy and the charging of high-voltage capacitors in preparation for shock delivery based on a predetermined set of criteria. In one embodiment, the inventive system operates in an ATP During Capacitor Charging (ATP-DCC) mode wherein all, or substantially all, of the ATP therapy is delivered during charging of the high-voltage capacitors. Based on evaluation of the predetermined set of criteria, the system may switch to an additional ATP Before Capacitor Charging (ATP-BCC) mode, wherein substantially all of the ATP therapy is delivered prior to charging of the high-voltage capacitor. According to one aspect of the invention, the predetermined set of criteria is based, at least in part, on the effectiveness of previously-delivered ATP therapy.

25 Claims, 9 Drawing Sheets

U.S. PATENT DOCUMENTS

| | | |
|---|---|---|
| 5,251,624 A | 10/1993 | Bocek et al. |
| 5,318,591 A * | 6/1994 | Causey et al. ............ 607/5 |
| 5,330,505 A | 7/1994 | Cohen |
| 5,458,619 A | 10/1995 | Olson |
| 5,554,174 A * | 9/1996 | Causey, III ............ 607/5 |
| 5,662,688 A | 9/1997 | Haefner et al. |
| 5,713,924 A | 2/1998 | Min et al. |
| 5,913,550 A | 6/1999 | Watanuki |
| 6,167,308 A | 12/2000 | DeGroot |
| 6,400,986 B1 | 6/2002 | Sun et al. |
| 6,718,204 B2 | 4/2004 | DeGroot et al. |

* cited by examiner

US 8,170,663 B2

METHOD AND APPARATUS TO CONTROL DELIVERY OF HIGH-VOLTAGE AND ANTI-TACHY PACING THERAPY IN AN IMPLANTABLE MEDICAL DEVICE

RELATED APPLICATION

This application is a continuation of U.S. patent application Ser. No. 10/810,449 filed on Mar. 26, 2004 now abandoned, entitled "METHOD AND APPARATUS TO CONTROL DELIVERY OF HIGH-VOLTAGE AND ANTI-TACHY PACING THERAPY IN AN IMPLANTABLE MEDICAL DEVICE", to DeGroot et al., incorporated herein by reference in its entirety, which is a continuation of U.S. patent application Ser. No. 09/918,244, filed Jul. 30, 2001, now U.S. Pat. No. 6,718,204 granted on Apr. 6, 2004, entitled "METHOD AND APPARATUS TO CONTROL DELIVERY OF HIGH-VOLTAGE AND ANTI-TACHY PACING THERAPY IN AN IMPLANTABLE MEDICAL DEVICE", to DeGroot et al., incorporated herein by reference in its entirety.

FIELD OF THE INVENTION

The present invention relates generally to utilizing implantable cardioverters (ICDs) to detect and/or treat ventricular tachyarrhythmias (rapid heart rhythms); and, more specifically, to preserving battery longevity of an ICD by tracking the success rate(s) of anti-tachycardia pacing (ATP) therapy.

BACKGROUND OF THE INVENTION

Implantable cardioverter-defibrillator (ICD) art has long distinguished ventricular tachyarrhythmias by rate and type. Ventricular tachycardias (VTs) generally are those arrhythmias with rates between 150 and 250 bpm. These rhythms can be further differentiated by their ECG configuration as either monomorphic or polymorphic. Arrhythmias with rates above the upper VT range, and up to approximately 350 bpm, are often termed flutter waves. Chaotic waveforms at rates higher than 350 bpm are classified as ventricular fibrillation (VF).

To treat each type of arrhythmia with an appropriate therapy, ICDs have been equipped with "tiered therapies". Such devices are generally referred to as Pacer-Cardioverter-Defibrillators (PCDs). PCDs generally differentiate arrhythmias by rates, with programmable therapies to treat a respective type of detected arrhythmia(s). In such devices, the less-dangerous arrhythmias such as VT are treated by delivering a series of low-power pacing pulses to the heart at a relatively high rate. This therapy is often referred to as anti-tachyarrhythmia pacing therapy (ATP). In contrast, more perilous arrhythmias such as VF are often treated using a more aggressive shock therapy. For example, many PCDs may be programmed to first treat a VT with low-power ATP and then, if the VT progresses to ventricular flutter or fibrillation, deliver one or more high-power cardioversion or defibrillation shocks.

As may be evident from the foregoing discussion, high-voltage shocks are more effective at treating VT than ATP. For this reason, VTs having rates above 200 bpm are often treated by high-energy shocks when, in fact, they are monomorphic VTs that can be treated by low-energy ATP therapy. The more aggressive treatment is selected because most clinicians prefer a fast, immediate solution rather than waiting to determine whether ATP therapy will terminate the rhythm prior to delivering the high-voltage shock, possibly resulting in patient syncope. As a result, some patients must unnecessarily endure the pain of receiving a high-voltage shock delivery when painless ATP could have successfully terminated the rhythm.

Preventing the unnecessary delivery of high-voltage shocks has long been recognized as a very desirable goal. As a result, monitoring the rhythm during the charging of the high-voltage capacitors in preparation for shock delivery has been proposed. For example in U.S. Pat. No. 4,949,719, issued to Pless et al, and U.S. Pat. No. 5,191,884 issued to Gilli et al, the implanted device monitors heart rhythm during charging to determine whether the arrhythmia has spontaneously terminated and aborts the charging of the output capacitors if the rhythm has returned to normal.

Another approach to this issue is found in U.S. Pat. No. 5,318,591, issued to Causey et al., and incorporated herein by reference in its totality. The '591 patent teaches a three-tiered progressive approach using ATP as a first recourse, followed by a cardioversion pulse in the event ATP failed, with a defibrillation shock to be delivered if cardioversion also failed. The ICD begins charging its high-powered capacitors in parallel with the application of the ATP therapy. In addition, this charging may also start in parallel with the verification interval immediately following the previous therapy, during which time the ICD attempts to verify arrhythmia termination.

Numerous other patents describe ATP pacing including U.S. Pat. No. 5,193,536, issued to Mehra, U.S. Pat. No. 5,458,619 issued to Olson, U.S. Pat. No. 6,167,308, issued to DeGroot, and U.S. Pat. No. 6,178,350, issued to Olson, et al. This last patent, although it applies to atrial tachyarrhythmias, is of particular interest because of the manner in which the described system monitors for the continuing presence or absence of an atrial tachycardia (AT).

Other patents describe in more detail systems that involve the analysis of the sequence and timing of atrial and ventricular events prior to the selection of a therapy. Such patents include U.S. Pat. No. 5,205,283 issued to Olson, U.S. Pat. No. 5,193,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al.

In the patents listed above, one or two basic strategies are generally followed. A first strategy is to associate each type of arrhythmia with a predetermined set of criteria. Next, a patient's heart rhythm is monitored to identify a heart event, including intervals and/or rates associated with the event. This information is then compared against the various criteria sets to analyze the likelihood that the event may be characterized as a specific types of arrhythmia. Monitoring continues until one of the criteria sets is met, resulting in detection and diagnosis of the arrhythmia.

A second strategy used in the identification of a heart rhythm involves defining a set of criteria for events, event intervals and event rates which is generally indicative of a group of arrhythmias. After the criteria is met, the preceding and/or subsequent events are analyzed to determine which specific arrhythmia is present.

Typically and to summarize, many implantable anti-tachycardia pacemakers have the capability of providing a variety of anti-tachycardia pacing regimens. Normally, these regimens are applied according to a pre-programmed sequence, such as burst or ramp therapies among others. Each therapy extends over a series of a predetermined number of pacing pulses. After the series of pacing pulses is delivered, the devices check to determine whether the series of pulses was effective in terminating the detected tachyarrhythmia. Termination is generally confirmed by a return to sinus rhythm, for example, identified by a sequence of a predetermined number of spontaneous depolarizations separated by greater than a defined interval. In the absence of detected termination, the PCD applies more aggressive therapies such as synchronized cardioversion pulses or defibrillation shocks. While the delivery of ATP in some cases makes shock therapy unnecessary, a further reduction in the frequency of shock delivery is still desirable.

Applying an electrical pulse to the heart, whether a pacing pulse or a shock, requires charging of one or more output capacitors. Generally, the amount of energy required to deliver ATP is low. This type of therapy may therefore be delivered by a low-power output circuit relatively quickly. On the other hand, high-power shocks require a set of high-voltage capacitors that may require several seconds to reach a fully-programmed charge. As stated above, when a tiered therapy approach is utilized, both of these therapies may be used to "break" the tachyarrhythmia. That is, first ATP is delivered. During this time, the high-voltage capacitors may be charged so that if ATP fails to break the VT, a high-voltage shock may be delivered soon thereafter. If the VT is terminated by ATP, the charged high-voltage capacitors must abort delivery and internally "leak off" the stored energy in the capacitors, which depletes battery power. This can significantly shorten the life of the implanted device.

What is needed, therefore, is a method and apparatus to deliver successful ATP therapy without needlessly depleting battery resources.

SUMMARY OF THE INVENTION

The current invention proposes a novel system and method that addresses the foregoing and other problems associated with current ATP-delivery devices. The invention controls the time between delivering ATP therapy and the charging of high-voltage capacitors in preparation for shock delivery. This control is performed based on a predetermined set of criteria. In one embodiment, the inventive system may operate in an ATP During Capacitor Charging (ATP-DCC) mode. In this mode, all, or substantially all, of the ATP therapy is delivered during charging of the high-voltage capacitors. The system may switch to an additional ATP Before Capacitor Charging (ATP-BCC) mode, wherein all, or substantially all, of the ATP therapy is delivered prior to charging of the high-voltage capacitor. This switch occurs based on the predetermined set of criteria.

According to one aspect of the invention, the predetermined set of criteria is based, at least in part, on the effectiveness of previously-delivered ATP therapy. In one embodiment, mode switching from ATP-DCC to ATP-BCC mode occurs after a predetermined successful number of ATP therapy sessions are delivered while in ATP-DCC mode. A successful ATP therapy session is defined as a session that terminates a predetermined abnormal cardiac rhythm such as ventricular tachycardia (VT). Conversely, mode switching from operation in ATP-BCC to ATP-DCC mode occurs after a predetermined unsuccessful number of ATP therapy sessions are delivered while in ATP-BCC mode, wherein an unsuccessful ATP therapy session fails to terminate a predetermined abnormal cardiac rhythm.

The predetermined number of ATP therapy sessions used to initiate the mode switching may involve consecutive therapy sessions, a number X of Y therapy sessions, a number of X therapy sessions during a predetermined time, or any other measure of a number of therapy sessions that can be used for this purpose.

According to an additional aspect of the invention, waveform morphology and cardiac cycle length may be used to analyze various cardiac rhythms. This analysis is then used to define the criteria used to initiate mode switching. In one embodiment, the predetermined number of ATP therapy sessions used to trigger mode switching from ATP-DCC to ATP-BCC mode or vice versa is specific to a predetermined type of cardiac rhythm. Alternatively, or additionally, a change in cardiac rhythms occurring within the heart can also trigger mode switching. For example, a change in the type of VT being detected in the heart can trigger a switch from ATP-BCC to ATP-DCC mode.

Frequency of occurrence of predetermined cardiac rhythms may also be used to trigger a mode switch. In one embodiment, operation transitions from ATP-DCC to ATP-BCC mode or vice versa in response to the detection of a predetermined number of VT episodes detected within a predetermined period of time, wherein the predetermined period of time and/or the number of episodes occurring with the period of time may be programmable. This is important since the frequency of VT episodes varies among patients. While some patients have infrequent episodes, other patients have "VT storms", wherein a large number of episodes may occur within a very short time period. By programming these parameters based on patient history, device operation is tailored to individual patient needs.

Many other embodiments are possible within the context of the current invention. In one embodiment, operation transitions from ATP-DCC to ATP-BCC or vice versa based on episode duration. That is, those episodes with a shorter episode duration than a programmable value are considered to be a result of successful ATP therapy. Conversely, episodes with an episode duration longer than the programmable value are counted as ATP failures. The successes and failures may then be counted in a manner similar to that described above to invoke the mode changes. In yet another embodiment, a switch from ATP-DCC to ATP-BCC can be based on a simple episode counter, regardless of the success or failure of the ATP therapy, although this is a less preferred method.

According to yet another aspect of the invention, ATP therapy may be disabled entirely after a predetermined number of failed ATP attempts while operating in ATP-BCC or ATP-DCC modes. Other aspects of the invention will become apparent to those skilled in the art from the following description and the accompanying drawings.

DETAILED DESCRIPTION OF THE DRAWINGS

Figure 1:
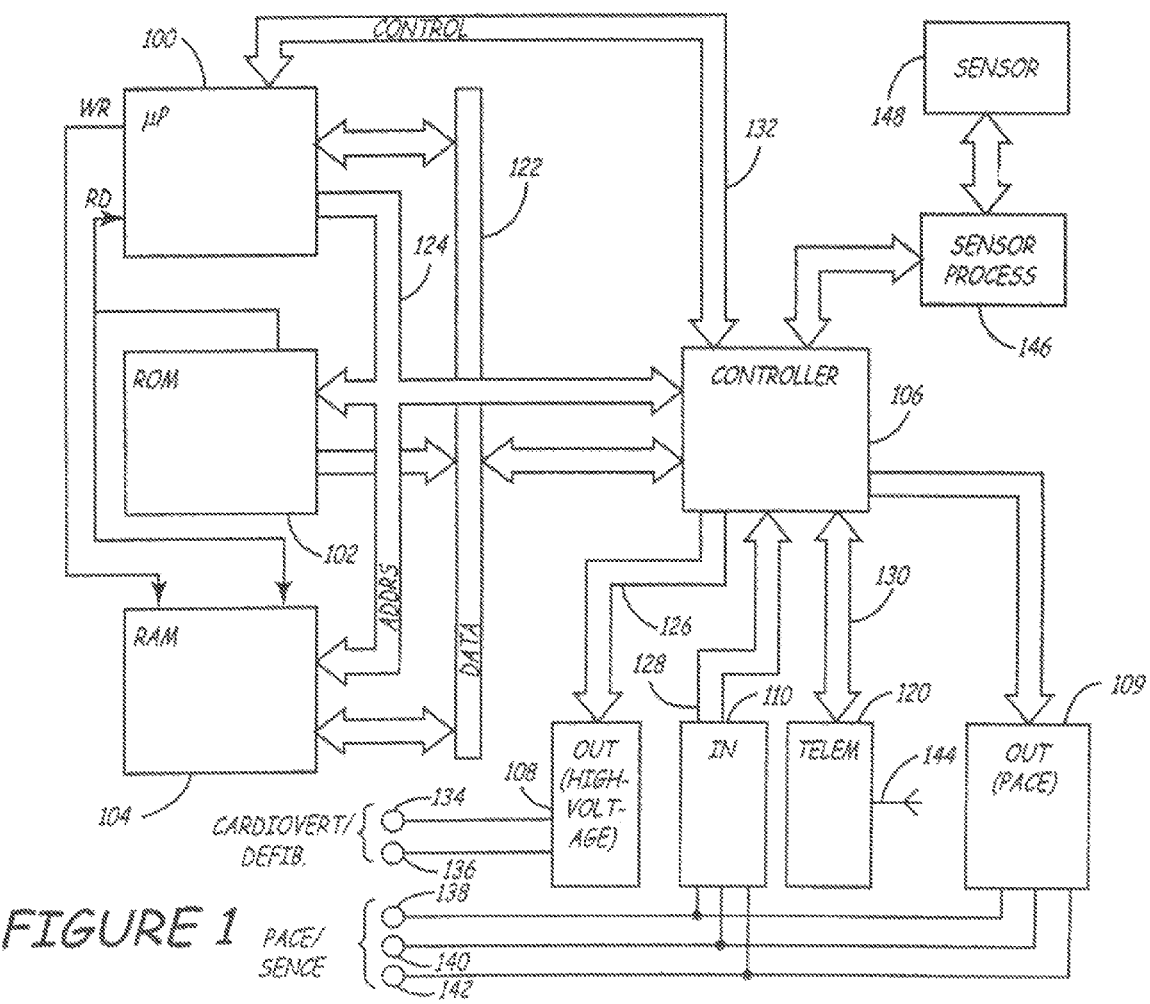
FIG. 1 is a block, functional diagram of an illustrative embodiment of a cardioverter/pacemaker according to the present invention.

FIG. 1 is a block functional diagram of an illustrative embodiment of a cardioverter/pacemaker that may be employed according to the present invention. As illustrated, the device is embodied as a microprocessor based stimulator. However, other digital circuitry embodiments and analog circuitry embodiments are also believed to be within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,593, issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. Similarly, while the device of FIG. 1 takes the form of a ventricular pacemaker/cardioverter, the present invention may also be usefully employed in a device having atrial pacing and cardioversion capabilities. FIG. 1 should thus be considered illustrative, rather than limiting with regard to the scope of the invention.

The primary elements of the apparatus illustrated in FIG. 1 are a microprocessor 100, read-only memory (ROM) 102, random-access memory (RAM) 104, a digital controller 106, an input amplifier circuit 110, two output circuits 108 and 109, and a telemetry/programming unit 120. Read-only memory stores the basic programming for the device, including the primary instruction set defining the computations performed to derive the various timing intervals employed by the cardioverter. RAM 104 generally serves to store variable control parameters, such as programmed pacing rate, programmed cardioversion intervals, pulse widths, pulse amplitudes, and so forth which are programmed into the device by the physician. Random-access memory 104 also stores derived values, such as the stored time intervals separating tachyarrhythmia pulses and the corresponding high-rate pacing interval.

Controller 106 performs all of the basic control and timing functions of the device. Controller 106 includes at least one programmable timing counter, which is initiated upon detection of a ventricular contraction, and which times intervals thereafter. This counter is used to generate the basic timing intervals used to deliver anti-tachy pacing (ATP) pulses, and to measure other intervals used within the context of the current invention. On time-out of the pacing escape interval or in response to a determination that a cardioversion or defibrillation pulse is to be delivered, controller 106 triggers the appropriate output pulse from high-voltage output stage 108, as discussed below.

Following generation of stimulus pulses, controller 106 may be utilized to generate corresponding interrupts on control bus 132, waking microprocessor 100 from its "sleep" state, allowing it to perform any required mathematical calculations, including all operations associated with evaluation of return cycle times and selection of anti-tachyarrhythmia therapies according to the present invention. The timing/counter circuit in controller 106 also may also control timing intervals such as ventricular refractory periods, as is known in the art. The time intervals may be determined by programmable values stored in RAM 104, or values stored in ROM.

Controller 106 may also generate interrupts for microprocessor 100 on the occurrence of sensed ventricular depolarizations or beats. On occurrence of a sensed ventricular depolarization, in addition to an interrupt indicating its occurrence placed on control bus 132, the then-current value of the timing/counter within controller 106 is placed onto data bus 122. This value may be used by microprocessor 100 in determining whether a tachyarrhythmia is present, and further, in determining the intervals separating individual tachyarrhythmia beats.

Output stage 108 contains a high-output pulse generator capable of generating cardioversion pulses of at least 0.1 joules, to be applied to the patient's heart via electrodes 134 and 136, which are typically large surface area electrodes mounted on or in the heart, or located subcutaneously. Other electrode configurations may also be used, including two or more electrodes arranged within and around the heart. Typically the high output pulse generator includes one or more high-voltage capacitors, a charging circuit, and a set of switches to allow delivery of monophasic or biphasic cardioversion or defibrillation pulses to the electrodes employed.

In addition to output circuit 108, output circuit 109 is provided to generate pacing pulses. This circuit contains a pacing pulse generator circuit that is coupled to electrodes 138, 140 and 142, and which are employed to accomplish cardiac pacing, including ATP pacing pulses, by delivery of a electrical stimulation between electrode 138 and one of electrodes 140 and 142. Electrode 138 is typically located on the distal end of an endocardial lead, and is typically placed in the apex of the right ventricle. Electrode 140 is typically an indifferent electrode mounted on, or adjacent to, the housing of the cardioverter defibrillator. Electrode 142 may be a ring or coil electrode located on an endocardial lead slightly proximal to the tip electrode 138, or it may be another electrode positioned inside or outside the heart. Output circuit 108 may be controlled by control bus 126, which allows the controller 106 to determine the time, amplitude and pulse width of the pulse to be delivered. This circuit may also determine which electrode pair will be employed to deliver the pulse.

Sensing of ventricular depolarizations (beats) is accomplished by input amplifier 110, which is coupled to electrode 138 and one of electrodes 140 and 142. Signals indicating both the occurrence of natural ventricular beats and paced ventricular beats are provided to the controller 106 via bus 128. Controller 106 passes data indicative of the occurrence of such ventricular beats to microprocessor 100 via control bus 132 in the form of interrupts, which serve to wake up microprocessor 100. This allows the microprocessor to perform any necessary calculations or to update values stored in RAM 104.

Optionally included in the device is one or more physiologic sensors 148, which may be any of the various known sensors for use in conjunction with implantable stimulators. For example, sensor 148 may be a hemodynamic sensor such as an impedance sensor as disclosed in U.S. Pat. No. 4,865,036, issued to Chirife or a pressure sensor as disclosed in U.S. Pat. No. 5,330,505, issued to Cohen, both of which are incorporated herein by reference in their entireties. Alternatively, sensor 148 may be a demand sensor for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties. Sensor processing circuitry 146 transforms the sensor output into digitized values for use in conjunction with detection and treatment of arrhythmias.

External control of the implanted cardioverter/defibrillator is accomplished via telemetry/control block 120 that controls communication between the implanted cardioverter/pacemaker and an external programmer. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

Figure 2:
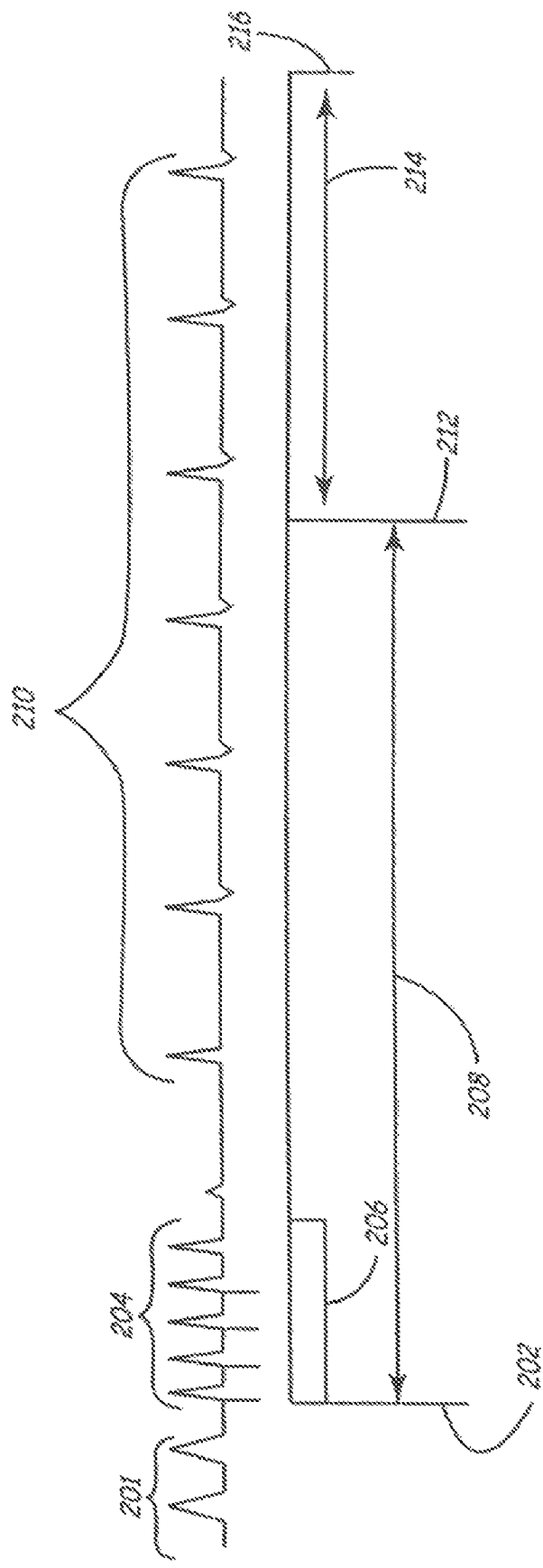
FIG. 2 is an illustration of ATP-DCC therapy resulting in a charge drain/dump.

FIG. 2 is a timing diagram illustrating operation of the current inventive system in ATP During Capacitor Charging (ATP-DCC) mode. After detection of a VT cardiac rhythm 201, capacitor charging 208 and ATP therapy delivery 204 may begin substantially simultaneously. High-rate VT 201, which in one embodiment is defined to include rhythms between 185 and 260 beats per minute (bpm), is treated by one sequence of Burst or Ramp or other type ATP-DCC therapy 204 that may extend for a predetermined period of time 206, or alternatively, for a predetermined number of pacing pulses. In this case, ATP-DCC therapy causes the VT rhythm to terminate, or "break", so that a normal sinus rhythm 210 is resumed.

When operation is occurring in ATP-DCC mode, all, or substantially all, of the ATP therapy is delivered while capacitor charging occurs. FIG. 2 shows charging 208 of high-voltage capacitors extending until charge time end 212 in preparation for delivery of a shock, if necessary. This shock may or may not be delivered at time 216, depending on whether normal sinus rhythm 210 has resumed. If it is determined that shock therapy is necessary, the shock will be delivered after synchronization with cardiac depolarizations has been completed during time 214. This synchronization attempts to deliver the shock at the appropriate time during the cardiac rhythm.

As noted above, ATP-DCC therapy may cause the VT rhythm to break. This break generally occurs in two ways. A "type 1" break occurs almost immediately after the last pacing pulse of an ATP therapy. In contrast, a "type 2" break involves several extra VT depolarizations following the last pacing pulse. Thus with a type 2 break, the ICD detection algorithm may not detect the return to normal sinus rhythm in time to prevent an unneeded shock delivery. Even in the case of a type 1 break, the detection of successful termination requires that the capacitors abort their charge.

In the case of either type 1 or type 2 breaks discussed above, the device battery is drained or dumped of a certain percentage of its power even though ATP therapy is successful. In an ICD device capable of delivering between 100-150 full-energy shocks, a patient experiencing ten ATP-terminated episodes during any one follow-up period drains up to ten percent of the device battery power in a short amount of time if ATP-DCC is utilized. Moreover, this problem is not uncommon. Studies have shown that approximately fifteen percent of patients have more than ten episodes during a six-month period of time. Some patients have been known to exceed this number, potentially expending the battery supply during the first six months of implant.

Figure 3:
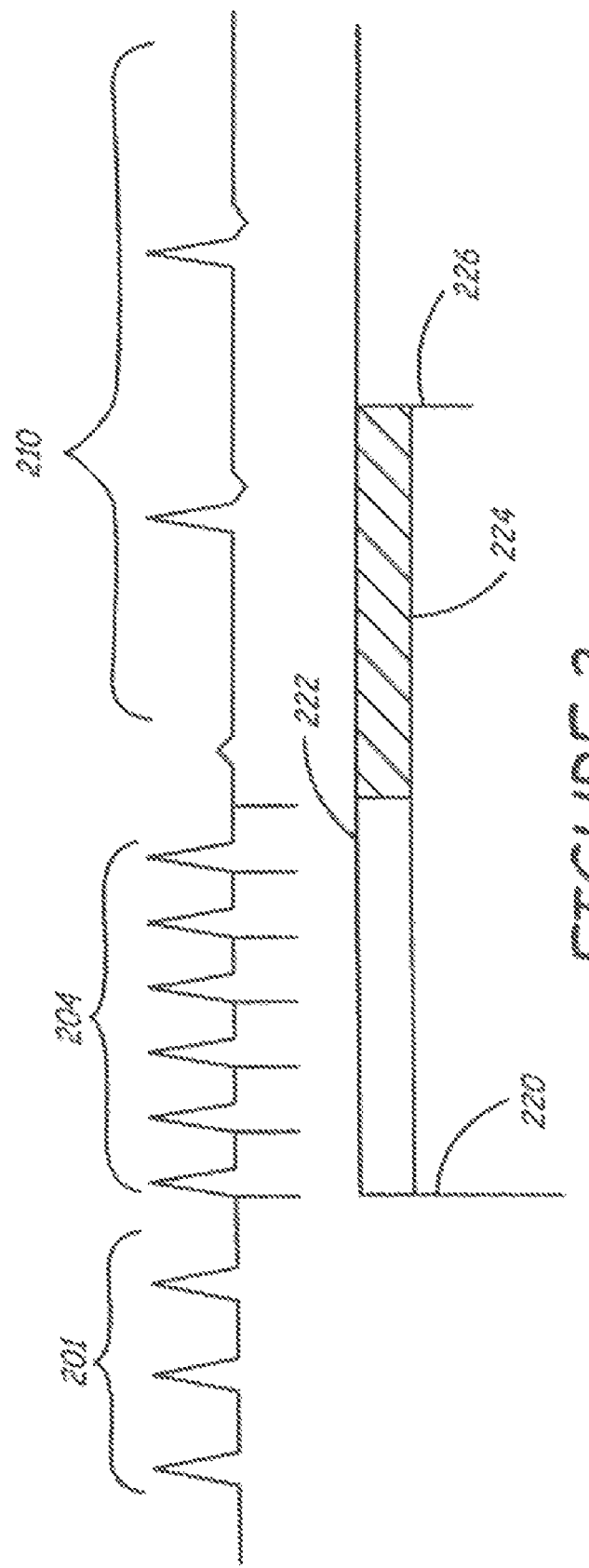
FIG. 3 illustrates a first embodiment of a successful ATP-BCC therapy resulting in aborting of capacitor charging.

FIG. 3 is a timing diagram illustrating operation of the current inventive system in ATP Before Capacitor Charging (ATP-BCC) mode. When operating in ATP-BCC mode, all, or substantially all, of the ATP therapy delivery occurs prior to capacitor charging. FIG. 3 illustrates delivery of ATP therapy 204 initiated at time 220 following detection of a VT episode 201. Therapy continues during time 222. In this case, ATP therapy returns the patient to normal sinus rhythm 210. The ICD device detects the break in VT by the change in cardiac rate as well as the return to normal sinus rhythm 210 during verification period 224. As a result, no charging of the high-voltage capacitors is initiated at time 226.

According to the current invention, operation of the ICD may transition from ATP-DCC mode shown in FIG. 2 to execution in ATP-BCC mode shown in FIG. 3 based on programmable criteria. In one embodiment, this "Charge Saver" function switches the ICD device operation from ATP-DCC to ATP-BCC mode after attaining a user-programmed consecutive number of ATP successes since the previous follow-up session. ATP therapy is generally considered successful when the VT breaks/aborts prior to shock delivery, although other criteria may be defined for determining the success of the ATP therapy. The device will revert back to ATP-DCC mode following a predetermined criteria, when may include a predetermined number of failures to break a VT in the ATP-BCC operational mode, as will further in reference to FIG. 4.

Figure 4:
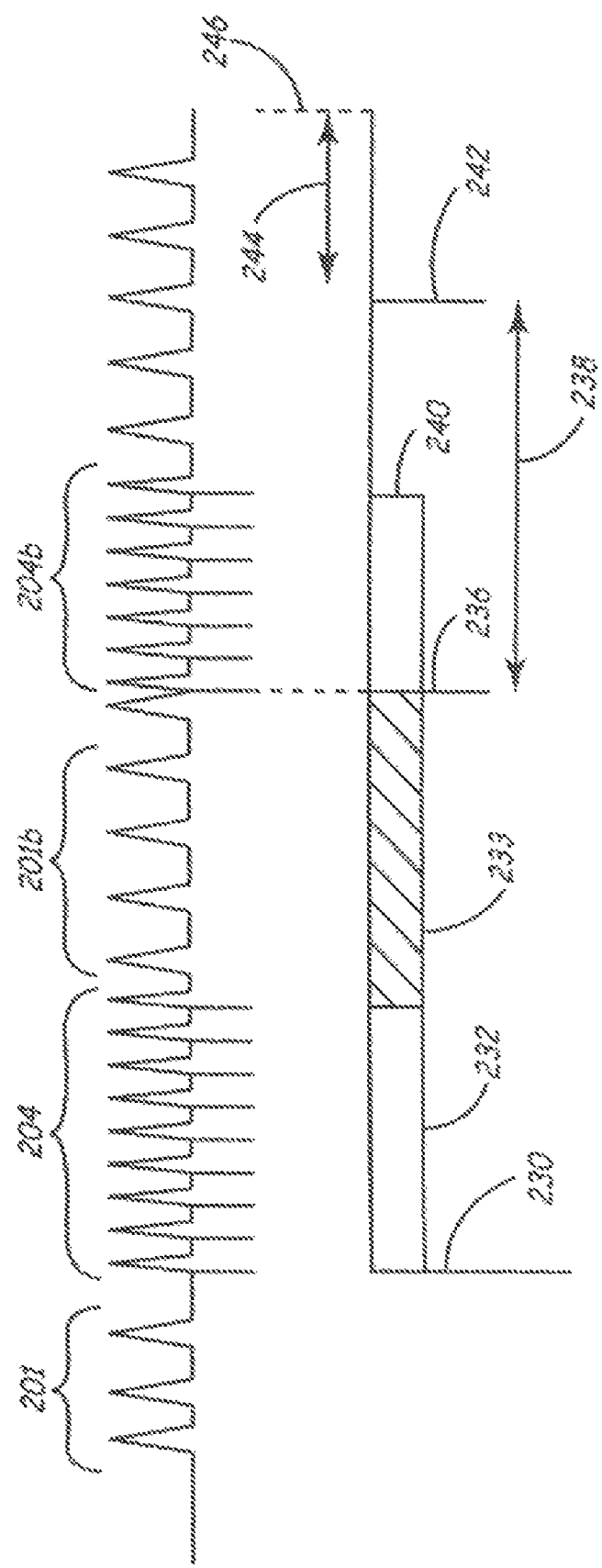
FIG. 4 is an illustration of ICD operation in the presence of a continuous VT that is not broken by ATP-BCC therapy.

FIG. 4 is a timing diagram illustrating an ongoing VT episode that fails to break following ATP-BCC therapy. ATP-BCC therapy 204 is delivered during time 232 following VT detection 201. Thereafter, verification period 233 confirms the ongoing VT episode 201b. Charging of high-voltage capacitors 238 begins substantially at time 236. According to one embodiment of the invention, a second sequence of ATP therapy 204b may be delivered during capacitor charging. Studies such as the Medtronic PainFREE $R_x$ study have shown that this additional ATP sequence has a low likelihood of accelerating the ventricular rate, and in fact, has the potential for terminating a VT episode.

Capacitor charging during time 238 has a variable duration, depending on the programmed energy value. At charge time end 242, a non-committed synchronization period 244 begins. During this synchronization period 244, the patient's cardiac rhythm is evaluated to locate an appropriate time to deliver a shock. The shock will be delivered at the end of the synchronization period unless it is determined that the VT episode has terminated. If the episode has terminated, the charge on the capacitors would be dumped or drained at the end of the capacitor charge time 238 or sometime thereafter.

According to another aspect of the current invention, if a predetermined number of episodes of VT are not terminated by ATP-BCC therapy such that shock delivery occurs as shown in FIG. 4, the system reverts from ATP-BCC mode to the ATP-DCC mode. This allows shock delivery to occur without delay following the unsuccessful delivery of ATP.

Figure 5:
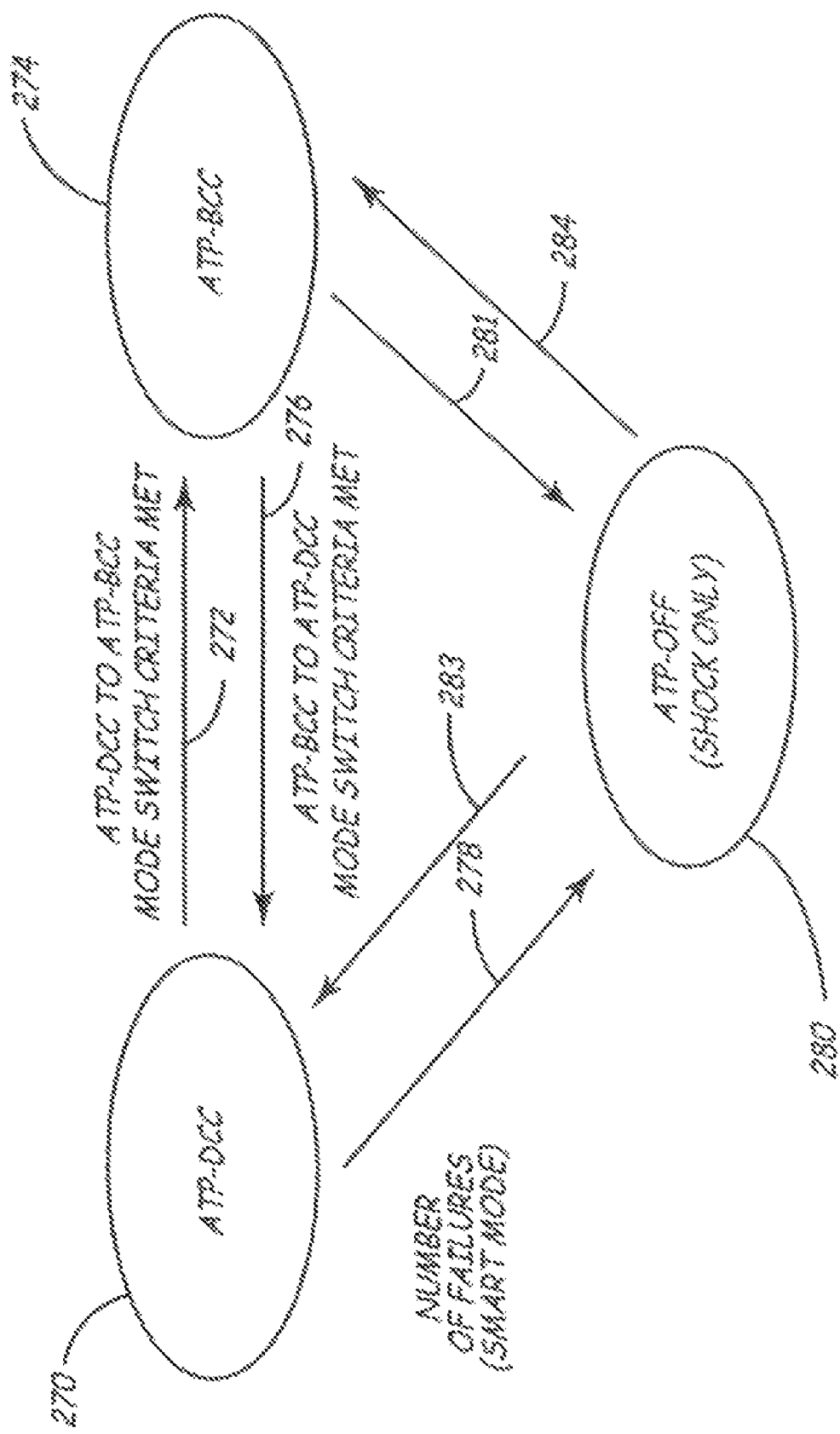
FIG. 5 is a flow diagram illustrating the transitions between various modes of operation in the current system.

FIG. 5 is a state diagram illustrating the manner in which the system transitions between ATP therapy modes. ICD devices are shipped from the factory with ATP-DCC mode and the Charge Saver feature enabled, as illustrated by state 270 as well as the Charge Saver feature. At the time of implant, the physician may choose whether to disable the Charge Saver feature. In one embodiment of the invention, other programmable parameters may be selected by the physician if the Charge Saver feature is enabled. These parameters may include the number of successful ATP-DCC therapy sessions that must be delivered prior to the automated activation of ATP-BCC mode, as will be discussed further below.

During operation with Charge Saver enabled and the system operating in ATP-DCC, a transition to ATP-BCC mode shown as state 274 may be triggered by the delivery of a predetermined number X ATP-DCC therapy sessions that succeed in breaking the VT rhythm. This transition is depicted by arrow 272. Conversely, when operating in ATP-BCC mode and after a predetermined number Y failed ATP-BCC therapy attempts, the system transitions to ATP-DCC mode as shown by arrow 276. As discussed above, in one embodiment of the invention, X and Y are programmable.

Alternatively, these numbers may be predetermined, non-programmable values. Finally, these numbers may represent consecutive ATP therapy sessions, or may involve a set of "S of T" therapy sessions. For example, a transition from ATP-DCC to ATP-BCC may be selected to occur if 4 of 5 ATP-DCC therapy sessions are determined to be successful.

Other trigger criteria may be used instead of, or in addition to, the above criteria to initiate a switch between ATP-DCC and ATP-BCC modes. In one embodiment, the system stores both cycle length (CL) and/or R-wave morphology of a VT rhythm to determine whether the type of VT currently being experienced is the same type of VT that occurred during a recently-detected episode or episodes. This is important since patients can exhibit different types of VT, each of which may respond differently to ATP therapy. If the characteristics of the current episode are the same as the previous episode, and the previous episode responded favorably to ATP-BCC therapy, the device remains in the ATP-BCC mode of operation upon detection of a break in rate. On the other hand, if the CL and/or R-wave morphology has changed, the system may be programmed to revert back to the ATP-DCC mode of operation.

According to the foregoing embodiment, different mode transition criteria may be specified for each type of VT rhythm. For example, a transition from ATP-DCC to ATP-BCC therapy may be triggered by M consecutive successful therapy sessions for a first type of VT. This same mode transition may be triggered by M' of N successful therapy sessions for a second type of VT. This allows therapies to be individually selected for different types of VT rhythms.

In yet another embodiment, the system mode-switching criteria takes into account VT frequency. As discussed above, some patients experience "VT storms" involving the occurrence of a large number of episodes within a short period of time, such as hours or even minutes. Such episodes, which usually involve VT rhythms having similar CLs and morphologies, may significantly impact battery resources. In this embodiment, the occurrence of a predetermined number of VT episodes in a predetermined time period may trigger a switch from ATP-DCC to ATP-BCC mode to save battery resources.

According to an alternative embodiment of the invention, a programmable threshold duration is used to detect VT storms. If two consecutive VT episodes occur within this predefined threshold duration, a count is incremented. If the count reaches a predetermined value within some larger programmable time period, a mode switch may be triggered. Once a mode switch to ATP-BCC mode occurs, continued operation in ATP-BCC mode may be predicated on obtaining a predetermined success rate using any of the mechanisms discussed above. Alternatively, another threshold time can be defined to track episode frequency in the ATP-BCC mode such that if the inter-episode duration exceeds this value, a transition back to ATP-DCC mode occurs.

If desired, waveform morphology criteria may be applied to VT storm detection. For example, VT episodes that are separated by longer periods of time such as weeks or months may involve different types of VT rhythms. Therefore, for all VT episodes, or just the VT episodes separated by a predetermined time period, mode-switch criteria may be individually specified for respective types of VT rhythms as discussed above.

Transition from ATP-DCC to ATP-BCC mode or vice versa could also be predicated on the length of an episode. For example, the episode length measured from first detection to the termination of a rhythm could be used as the mode-switching criteria. In one embodiment, longer episodes could trigger a transition to ATP-DCC mode.

According to yet another aspect of the invention, the detection of VT storms may trigger a patient alert (audible, vibratory or other). For example, the patient may be notified to contact a physician so that operating parameters of the system may be re-evaluated, and mode-switching conditions may be re-programmed, if necessary.

Another aspect of the invention relates to an optional programmable feature for disabling all modes of ATP. If this "Smart Mode" feature is enabled and a predetermined criteria is met, all ATP therapy is disabled. In one embodiment, this Smart Mode feature operates when execution is occurring in ATP-DCC mode and a predetermined number of failed therapy attempts is detected. This transition is shown by arrow 278 and state 280. The number of failed therapy attempts needed to trigger this transition may be programmable, or may be a predetermined number which is preferably "four". Thereafter, the ICD device will only deliver the programmed shock therapy. In another embodiment, this feature could also be provided when execution is occurring in ATP-BCC mode, as shown by arrow 281. In yet another embodiment, the switch from either ATP-BCC or ATP-DCC mode could be triggered by a VT rhythm or waveform morphology that meets a predetermined criteria. For instance, the transition to a mode wherein ATP is disabled may be triggered by detection of a fast VT rhythm that exceeds 250 bpm.

In one embodiment, after a transition occurs to a mode wherein ATP is disabled, shock therapy will continue until intervention is provided to re-activate the ATP-DCC mode. Such intervention may be provided, for example, during a subsequent follow-up session. In another embodiment, the system will continue operation in this mode until a defined criteria is met. For example, if the transition to the ATP-disabled mode occurs because of a fast VT rhythm, the system will revert back to the previous mode of operation after the fast VT episode has been terminated by the shock delivery, as shown by arrows 283 and 284.

Figure 6A:
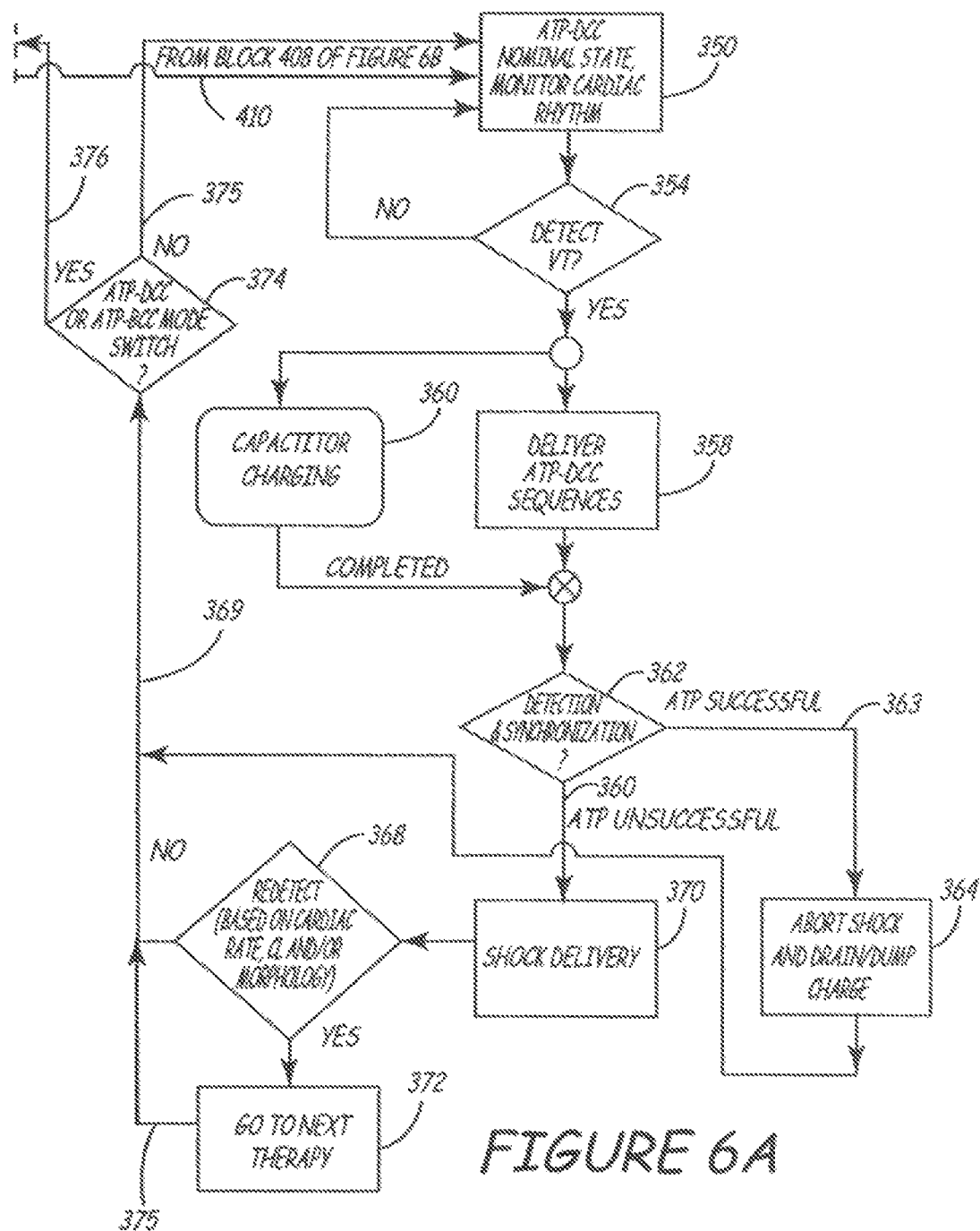
FIG. 6A and FIG. 6B, wherein arranged as shown in FIG. 6, are a flow diagram depicting ATP-DCC and ATP-BCC therapies, including mode switching.
Figure 6:
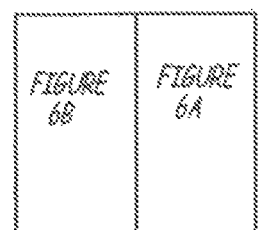
Figure 6B:
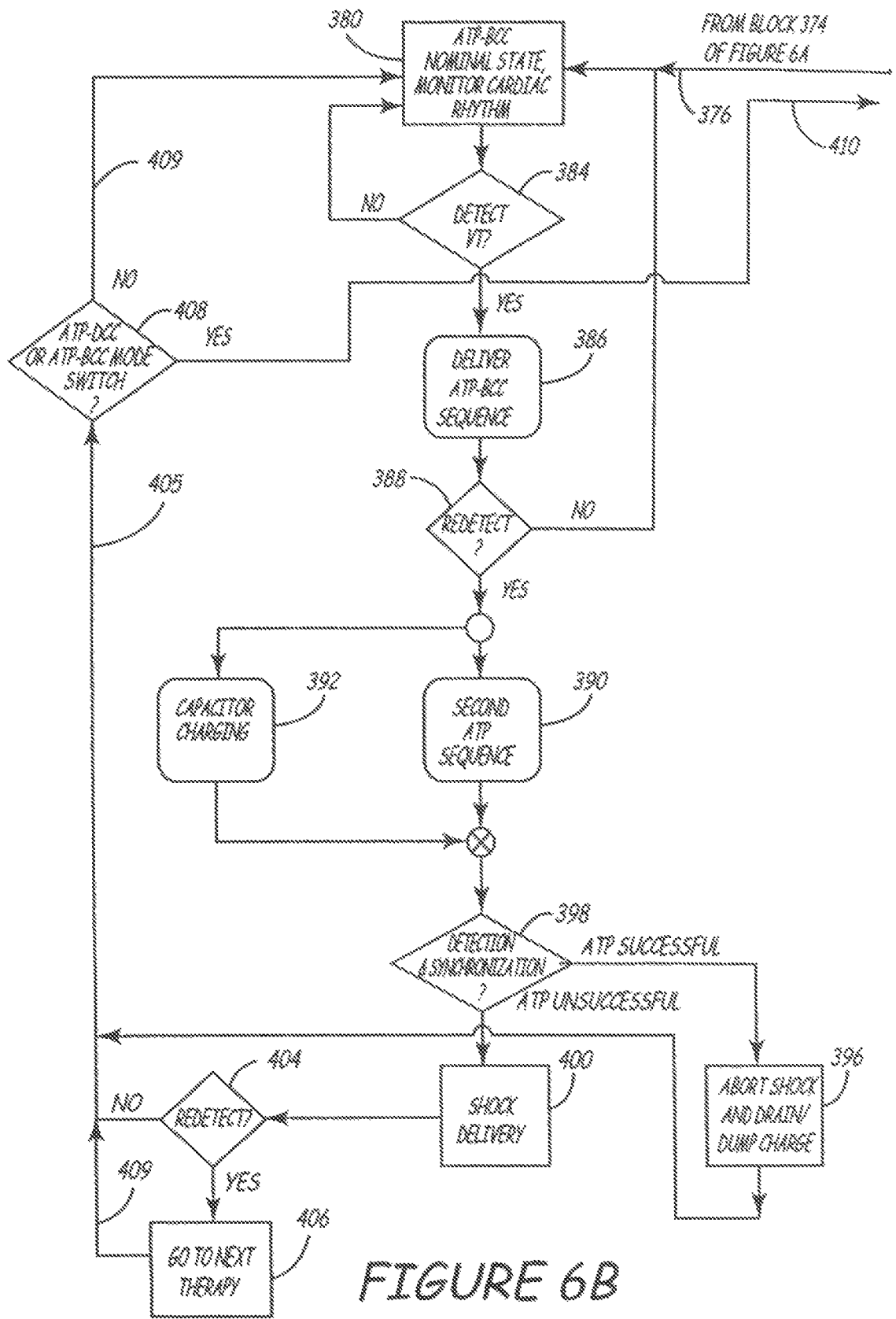

FIG. 6A and FIG. 6B, when arranged as shown in FIG. 6, are a flow diagram depicting ATP-DCC and ATP-BCC therapies, including mode switching. Beginning with FIG. 6A, a device such as the one shown in FIG. 1 is generally implanted with ATP-DCC mode enabled, although it maybe implanted with ATP-BCC mode enabled, if desired. The nominal ATP-DCC mode state is shown in block 350. In this state, the device is continuously monitoring for the presence of tachyarrhythmias, as illustrated in decision block 354. If a VT rhythm is detected, two operations are initiated. The first operation involves delivery of an ATP-DCC therapy sequence illustrated in block 358. The second operation relates to charging of the high-voltage capacitors, as shown in block 360.

Following completion of both capacitor charging and ATP therapy delivery, a synchronization period occurs, as shown in block 362. Synchronization is needed to determine an appropriate time within the occurring VT rhythm to deliver the shock, and to determine if the VT rhythm has terminated. When the system is synchronized, shock delivery will occur unless the system has first determined that the VT rhythm has been terminated. In this case, the device aborts shock delivery and dumps or drains the acquired capacitor charge, as shown by arrow 363 and block 364. If, on the other hand, ATP-DCC therapy was not unsuccessful, synchronization period 362 culminates in shock delivery. This is illustrated by arrow 360 and block 370.

After shock delivery, device circuitry determines whether VT is still present, as depicted in decision block 368. Several criteria may be used to make this determination, including cardiac rate, cycle length, R-wave morphology, and/or any other criteria known in the art for this purpose. If the VT has not terminated, the device begins the process of delivering the next programmed therapy as illustrated in block 372. Thereafter, processing continues with block decision block 374, as shown by arrow 375. If the VT is no longer present in block 368, however, the system continues directly to decision block 374 from decision block 368 via arrow 369.

If a mode switch is not indicated in block 374, operation continues in the nominal state illustrated by block 350. Otherwise, processing continues to block 380 of FIG. 6B, as shown by arrow 376. Block 380 represents the nominal ATP-BCC mode state of operation. In this state, the system monitors for the presence of tachyarrhythmias. When a tachyarrhythmia meets VT criteria, as shown in decision block 384, an ATP-BCC sequence is initiated, as illustrated in block 386. Upon completion of ATP-BCC sequence, the system determines whether the VT episode is still present in decision block 388. If ATP-BCC therapy has successfully terminated the VT, the system reverts to the nominal state illustrated in block 380. Because ATP therapy occurs prior to the start of battery charging, there is no high-voltage charge to be drained from the capacitor, with a resultant savings in battery resources.

Returning to block 388, if the VT episode is re-detected and meets VT criteria, a second ATP sequence may be initiated, as shown in block 390. Additionally, charging of high-voltage capacitors also begins, as illustrated in block 392. Following completion of this charging process, synchronization begins to determine an appropriate time to deliver the shock. When synchronization is complete in Block 398, shock delivery occurs as shown in block 400, unless it is sooner determined that the second ATP-BCC therapy session has successfully terminated the VT. In this case, the capacitor charge is drained, as depicted in step 396.

Upon completion of shock delivery, the device determines in block 404 whether VT is still present. As discussed above and shown in block 368, this may be accomplished by evaluating cardiac rate, cycle length, R-wave morphology, and/or any other criteria known in the art for this purpose. If the VT has not terminated i.e., VT is re-detected in block 404, the system begins the process of delivering the next programmed therapy in block 406. Thereafter, execution proceeds to decision block 408 where the system determines whether a mode switch should occur, as shown by arrow 409. Otherwise, if the VT was terminated, i.e., VT is not redetected in block 404, the system proceeds directly to decision block 408 via arrow 405. If a mode switch should occur, processing continues to FIG. 6A, as shown by arrow 410. If no mode switch is to occur, operation continues in the nominal state shown in block 380.

Figure 7:
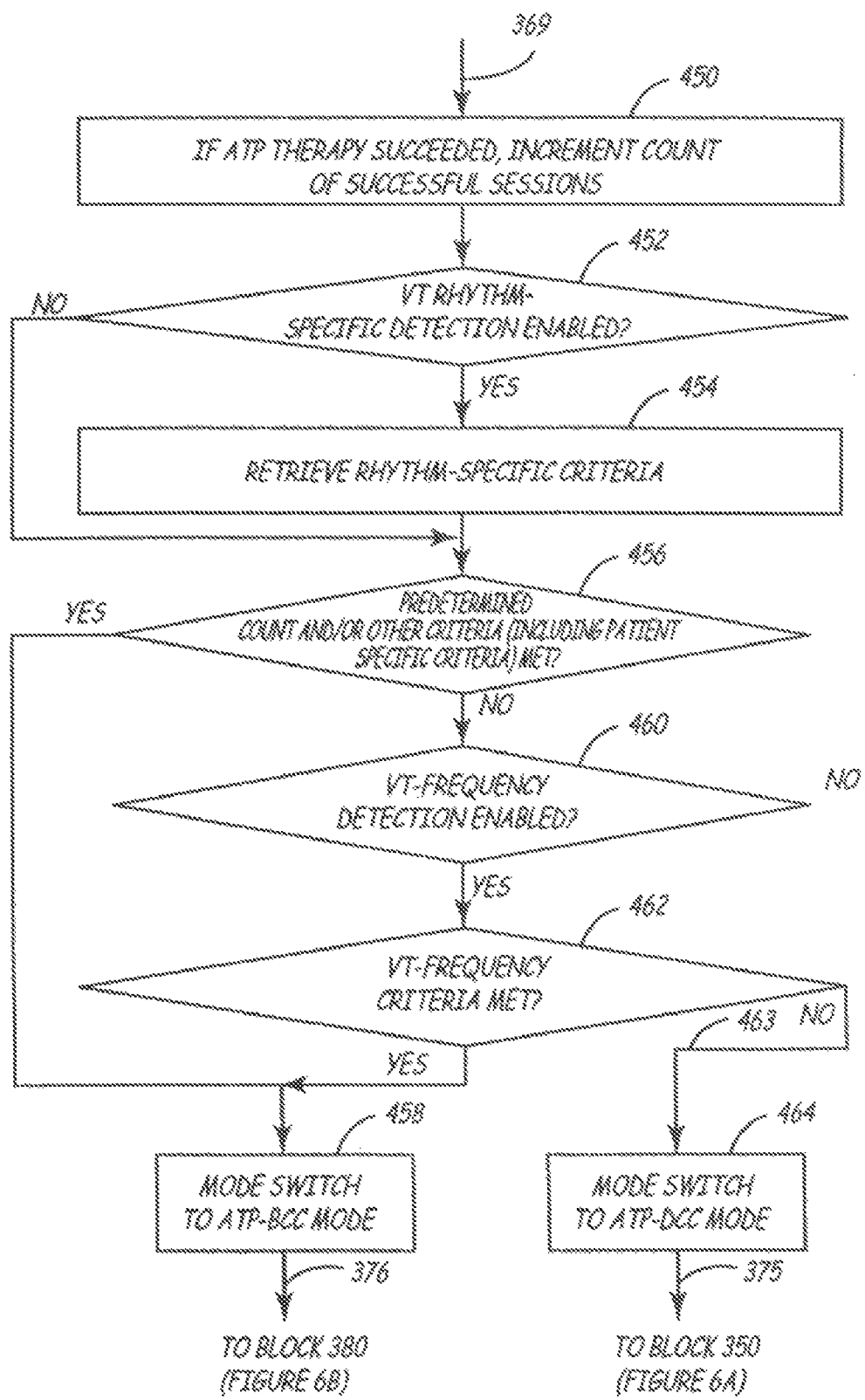
FIG. 7 is a flow diagram illustrating the ATP-DCC to ATP-BCC mode switch.

FIG. 7 is a flow diagram illustrating the ATP-DCC to ATP-BCC mode switch as shown in block 374 of FIG. 6A. Processing begins in block 450, where the count of successful ATP therapy sessions is incremented if the most-recently provided ATP therapy terminated the VT rhythm. Next, in block 452, it is determined whether rhythm-specific criteria will be used to make the mode-switch determination. As described above, it may be desirable to define specific criteria for the various types of VT rhythms, as may be identified by cycle length, and waveform morphology.

If rhythm-specific criteria will be utilized, the VT rhythm associated with the most recent VT episode is analyzed, and the corresponding criteria retrieved, as shown in block 454. Otherwise, the standard criterion is utilized. This criterion may be programmable, or a pre-set value.

After the criterion is selected, if necessary, the count of successful ATP therapy sessions is compared against the appropriate criteria in block 456 to determine whether a mode switch should be performed. It may be noted that this criteria may involve a consecutive number of successes, a predetermined number of successes in a predetermined period of time, or may instead require X of Y successes, as discussed above. Other criteria that do, or do not, involve a count of successful therapy-delivery sessions may be used instead of, or in addition to, the predetermined count criteria. For example, the duration of a VT episode may be utilized to trigger a mode switch to ATP-BCC mode, if desired. As will be discussed further below, this criteria may include patient-specific criteria. If the pre-defined criteria are met, the mode switch is performed in block 458. Processing then continues to block 380 of FIG. 6B.

If the predetermined criteria are not met in decision block 454, execution continues with block 460, where a determination is made as to whether VT-frequency monitoring is enabled so that VT storms may be detected. If so, a determination is made as to whether the VT-frequency criteria are met, as illustrated in block 462. This involves making a determination as to whether a predetermined number of VT episodes are detected in a specific period of time. Alternatively, an inter-episode threshold duration may be defined to detect VT storms in the manner discussed above. The detection may also take into consideration types of VT episodes, if desired. For example, separate running counts may be maintained for various types of VT episodes, with the types being determined by CL and waveform morphology. Each type of episode may also be associated with different criteria in a manner similar to that discussed. For example, a VT storm indication may be met if a first type of VT episode occurs X times in Y minutes, whereas a VT storm indication is met for a second type of VT episode occurring X' times in Y' minutes, and so on.

If any of the one or more VT-frequency criteria is met, a mode switch occurs, as indicated by block 458 and arrow 376. Otherwise, if VT-frequency detection is not enabled, or the VT-frequency criteria are not met, processing continues in ATP-DCC mode as illustrated by block 464 and arrow 375.

Figure 8:
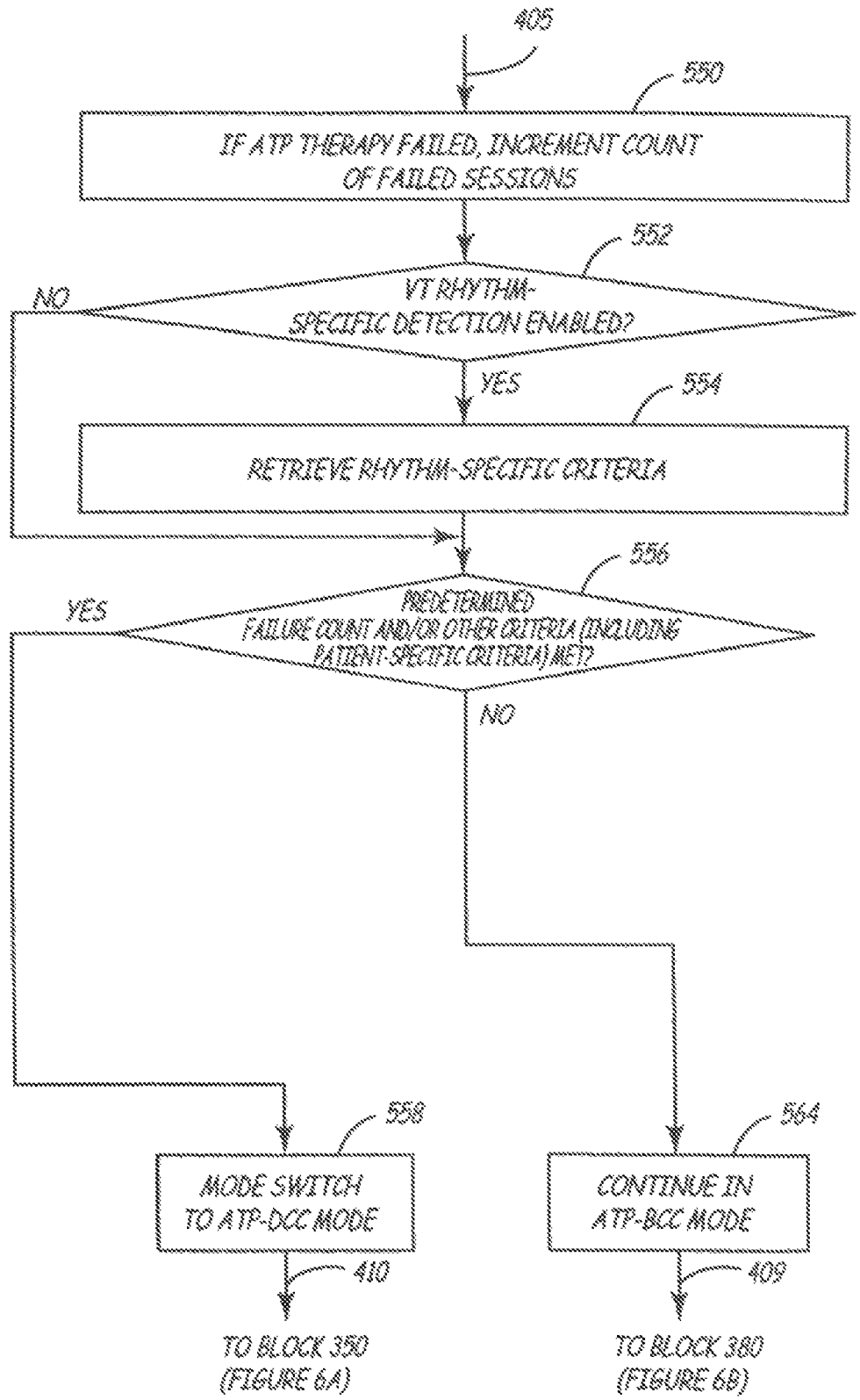
FIG. 8 is a flow diagram illustrating the ATP-BCC to ATP-DCC mode switch.

FIG. 8 is a flow diagram illustrating the ATP-BCC to ATP-DCC mode switch as shown in block 408 of FIG. 6B. Processing begins in block 550, where the count of unsuccessful ATP therapy sessions is incremented if the most-recently provided ATP therapy failed to terminate the VT rhythm. Next, in block 552, it is determined whether rhythm-specific criteria will be used to make the mode-switch determination. As described above, different criteria may be defined for different VT rhythms.

If rhythm-specific criteria will be utilized, the VT rhythm associated with the most recent VT episode is analyzed, and the corresponding criteria retrieved, as shown in block 554. Such rhythm-specific criteria may involve a mode switch from ATP-BCC to ATP-DCC mode based on the detection of a particular type of VT episode, for instance. In another instance, the rhythm-specific criteria may involve a count of a number a failed therapy attempts, for example.

If a rhythm-specific criteria are not to be utilized as determined in block 554, a standard criterion may be utilized. In either case, the appropriate criteria are used in block 556 to determine whether a mode switch should be performed. It may be noted that this criteria may involve a consecutive number of failed therapy attempts, may instead require X of Y failed therapy attempts, or may require a predetermined number of failures in a predetermined amount of time as discussed above. In one embodiment, a predetermined number of failed therapy attempts from the last patient medical check-up may be utilized as the trigger criteria. In another embodiment, the criteria may alternatively or additionally include conditions unrelated to failed therapy attempts, such as the occurrence of a particular type of rhythm, or a specific change in a type of rhythm, as noted above. This criteria may also include patient-specific conditions related to patient medical history. If this criteria met, the mode switch is performed in block 558. Processing then continues to block 380 of FIG. 6B. Otherwise, processing continues in block 564 in ATP-BCC mode.

As discussed above, many different types of criteria may be used to trigger a mode switch. In one embodiment, this criteria is programmable, and may be initially programmed and/or thereafter altered based on patient history. This allows system operation to be tailored for each patient. This could take into account, for example, a patient's individual response to ATP therapies. Programming can be accomplished, for example, using telemetry systems known in the art.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

What is claimed is:

1. A system for use in controlling electrical therapy delivered to a heart, comprising:
    a first circuit that is charged to deliver high-voltage electrical stimulation to the heart;
    a second circuit to deliver anti-tachy pacing (ATP) therapy to the heart; and
    a control circuit coupled to the first and second circuits to adjust a time of initiation of charging of the first circuit relative to a time of delivering ATP therapy by the second circuit for one delivery of ATP therapy relative to another delivery of ATP therapy.

2. The system of claim 1, wherein the control circuit is configured to operate in a first mode to charge the first circuit to deliver high-voltage electrical stimulation to the heart substantially simultaneously with delivery of ATP therapy to the heart by the second circuit, and a second mode to charge the first circuit to deliver high-voltage electrical stimulation to the heart substantially after delivery of ATP therapy to the heart by the second circuit.

3. The system of claim 2, wherein the control circuit is configured to transition between operating in the first mode and the second mode.

4. The system of claim 3, wherein the control circuit is configured to transition between operating in the first mode and the second mode based on at least one predetermined criteria.

5. The system of claim 4, and further including a storage device coupled to the control circuit to store the at least one predetermined criteria, and wherein the at least one predetermined criteria is programmable.

6. The system of claim 4, and further including at least one electrode coupled to the control circuit to sense cardiac rhythms, and a processing circuit coupled to the control circuit to analyze types of the cardiac rhythms, and wherein the at least one predetermined criteria takes into account the types of the cardiac rhythms occurring in the heart.

7. The system of claim 6, wherein the control circuit includes means for utilizing different values for the at least one predetermined criteria, and wherein the values are respectively associated with a type of cardiac rhythm occurring during delivery of ATP therapy.

8. The system of claim 4, wherein the at least one predetermined criteria includes criteria associated with a change in a type of cardiac rhythm occurring prior to the delivery of ATP therapy.

9. The system of claim 8, wherein the control circuit includes means for transitioning from the first mode to the second mode based on the criteria associated with a change in a type of cardiac rhythm occurring during the delivery of ATP therapy.

10. The system of claim 3, wherein the control circuit is configured to transition between operating in the first mode and the second mode based on the effectiveness of a previously delivery of ATP therapy by the second circuit.

11. The system of claim 3, wherein the control circuit is configured to transition from operating in the first mode and to operating in the second mode based on detection of a predetermined number of successful ATP therapy sessions, wherein a successful ATP therapy session terminates a predetermined abnormal cardiac rhythm.

12. The system of claim 3, wherein the control circuit is configured to transition between from operating in the second mode to operating in the first mode based on detection of a predetermined number of unsuccessful ATP therapy sessions, wherein an unsuccessful ATP therapy session fails to terminate a predetermined abnormal cardiac rhythm.

13. The system of claim 3, wherein the control circuit is configured to transition between operating in the first mode and the second mode based on a frequency of occurrence of a predetermined cardiac rhythm.

14. The system of claim 3, wherein the control circuit is configured to transition between the first mode and the second mode based on detection of a predetermined number of VT episodes.

15. The system of claim 3, wherein the control circuit is configured to transition between the first mode and the second mode based on detection of a predetermined number of VT episodes detected in a predetermined period of time.

16. The system of claim 3, wherein the control circuit is configured to transition between the first mode and the second mode based on a duration of a VT episode.

17. The system of claim 16, wherein the control circuit is configured to transition between the first mode and the second mode based on comparison of a duration of a VT episode to a predetermined value to determine whether a previously delivered ATP therapy was successful.

18. The system of claim 3, wherein the control circuit is configured to transition between operating in the first mode and the second mode in response to a length of an episode corresponding to a previously delivered ATP therapy.

19. A method for use in delivering electrical stimulation to a heart, comprising:
    delivering anti-tachy pacing (ATP) therapy to a patient's heart;
    charging a high-voltage capacitor in preparation to deliver high voltage electrical stimulation to the heart; and
    adjusting a time of initiation of charging the high-voltage capacitor in preparation to deliver high-voltage electrical stimulation to the heart in relation to a time of delivering the ATP therapy to the patient's heart for one delivery of ATP therapy relative to another delivery of ATP therapy.

20. The method of claim 19, wherein adjusting a time of charging the high-voltage capacitor in preparation to deliver high-voltage electrical stimulation to the heart in relation to a time of delivering the ATP therapy to the patient's heart comprises:

operating in a first mode to charge the first circuit to deliver high-voltage electrical stimulation to the heart substantially simultaneously with delivery of ATP therapy to the heart by the second circuit; and operating in a second mode to charge the first circuit to deliver high-voltage electrical stimulation to the heart substantially after delivery of ATP therapy to the heart by the second circuit.

21. The method of claim 20, further comprising:

transitioning between operating in the first mode and the second mode.

22. The method of claim 21, wherein transitioning between operating in the first mode and the second mode includes transitioning based on at least one predetermined criteria.

23. The method of claim 21, wherein transitioning between operating in the first mode and the second mode includes transitioning based on detection of at least one cardiac depolarization.

24. The method of claim 21, wherein transitioning between operating in the first mode and the second mode includes transitioning based on detecting a frequency of occurrence of a predetermined cardiac rhythm.

25. The method of claim 21, wherein transitioning between operating in the first mode and the second mode includes transitioning based on detecting a ventricular tachycardia (VT).

\* \* \* \* \*